US005485856A

United States Patent [19]
Buckland

[11] Patent Number: 5,485,856
[45] Date of Patent: Jan. 23, 1996

[54] HAND IMMOBILIGING AND POSITIONING APPARATUS FOR X-RAY EXAMINATIONS

[76] Inventor: Peter E. Buckland, 17835 NW. 63rd Ct., Miami, Fla. 33015

[21] Appl. No.: 231,235

[22] Filed: Apr. 22, 1994

[51] Int. Cl.⁶ ............................. A61G 15/00; A61F 5/37
[52] U.S. Cl. ............................................. 128/845; 128/879
[58] Field of Search .................................. 128/845, 878, 128/879, 880, 881, 882, 892, 877, 869, 846; 602/22, 21, 20, 5; 132/73, 285; 5/601, 623, 646, 647; 378/208, 180, 177, 175

[56] References Cited

U.S. PATENT DOCUMENTS

| | | | |
|---|---|---|---|
| 2,223,204 | 11/1940 | Carmichael | 132/73 |
| 2,566,852 | 9/1951 | Platt | 132/73 |
| 3,198,197 | 8/1965 | Van Halanger | 132/73 |
| 3,639,764 | 2/1972 | Olson et al. | 378/180 |
| 3,715,587 | 2/1973 | Burkhalter et al. | 250/50 |
| 3,746,332 | 7/1973 | Hakstian | 5/647 |
| 4,045,678 | 8/1977 | Rickard | 5/601 |
| 4,082,257 | 4/1978 | Strickland | 5/623 |
| 4,674,110 | 6/1987 | Eaton et al. | 378/208 |
| 4,858,903 | 8/1989 | Tari et al. | 5/623 |
| 4,915,331 | 4/1990 | Bicker et al. | 132/73 |
| 5,027,802 | 7/1991 | Donohue | 602/22 |
| 5,136,743 | 8/1992 | Pirela-Cruz | 5/647 |
| 5,140,998 | 8/1992 | Vickers | 128/880 |
| 5,295,948 | 3/1994 | Gray | 602/5 |
| 5,323,786 | 6/1994 | Juhasz | 128/845 |
| 5,327,912 | 7/1994 | Mally | 128/878 |

FOREIGN PATENT DOCUMENTS

| | | | |
|---|---|---|---|
| 3113685 | 10/1982 | Germany | 128/880 |

OTHER PUBLICATIONS

Brochure: Cone Instruments, vol. 10, 1992–3, p. 103.
Picker Health Care Products Buyer's Guide, vol. 6 p. 293.

*Primary Examiner*—Robert A. Hafer
*Assistant Examiner*—Michael O'Neill
*Attorney, Agent, or Firm*—Frank L. Kubler

[57] ABSTRACT

A hand immobilizing apparatus is provided for positioning the hand for intra-operative, antero-posterior and lateral views with minimal difficulty in reorienting the hand for each, and to isolate individual fingers for lateral views, so that the image of one finger is not superimposed over the image of an other finger. The apparatus includes a hand-receiving channel member made of radiolucent material. The channel member has a bottom wall joined to two opposing side walls and is sized so that the back of the hand can be placed flat against the bottom wall. The apparatus also includes a block of radiolucent material sized to fit closely between the channel side walls, to hold any single extended finger against the channel bottom wall for lateral examination. The remaining fingers rest against a side face of the block and are curled generally toward the palm of the hand. The block and channel side walls are provided with fastening means which are preferably contact-activated, such as hook and loop fasteners or an adhesive, to removably secure the block within the channel member against the isolated finger during examination. The palm of the hand is preferably held within the channel member by securing straps. The apparatus alternatively includes a stepped support plate having a stepped edge for placing within the channel member so that a single finger rests on each step. As a result, all fingers are laterally isolated simultaneously.

5 Claims, 6 Drawing Sheets

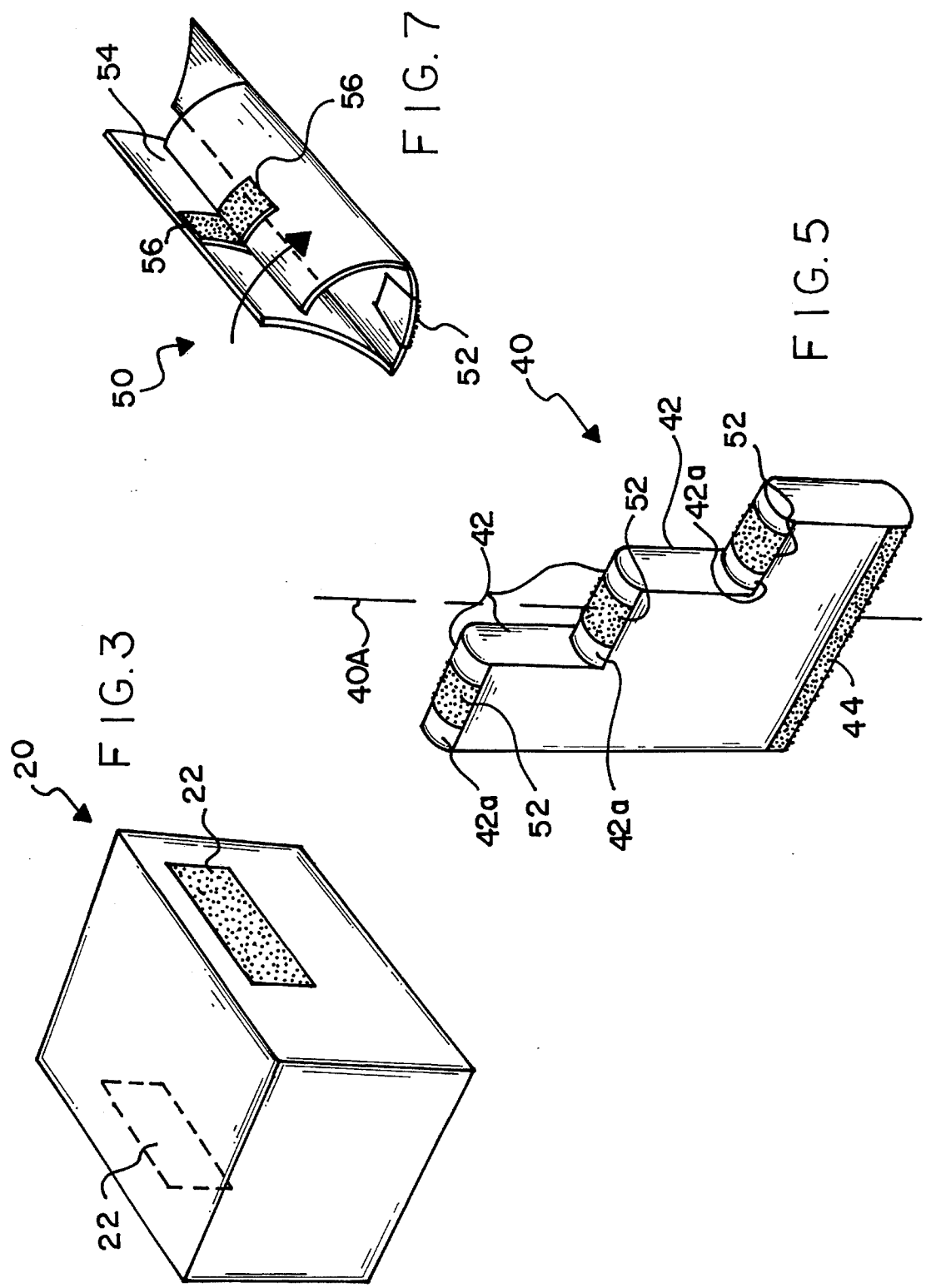

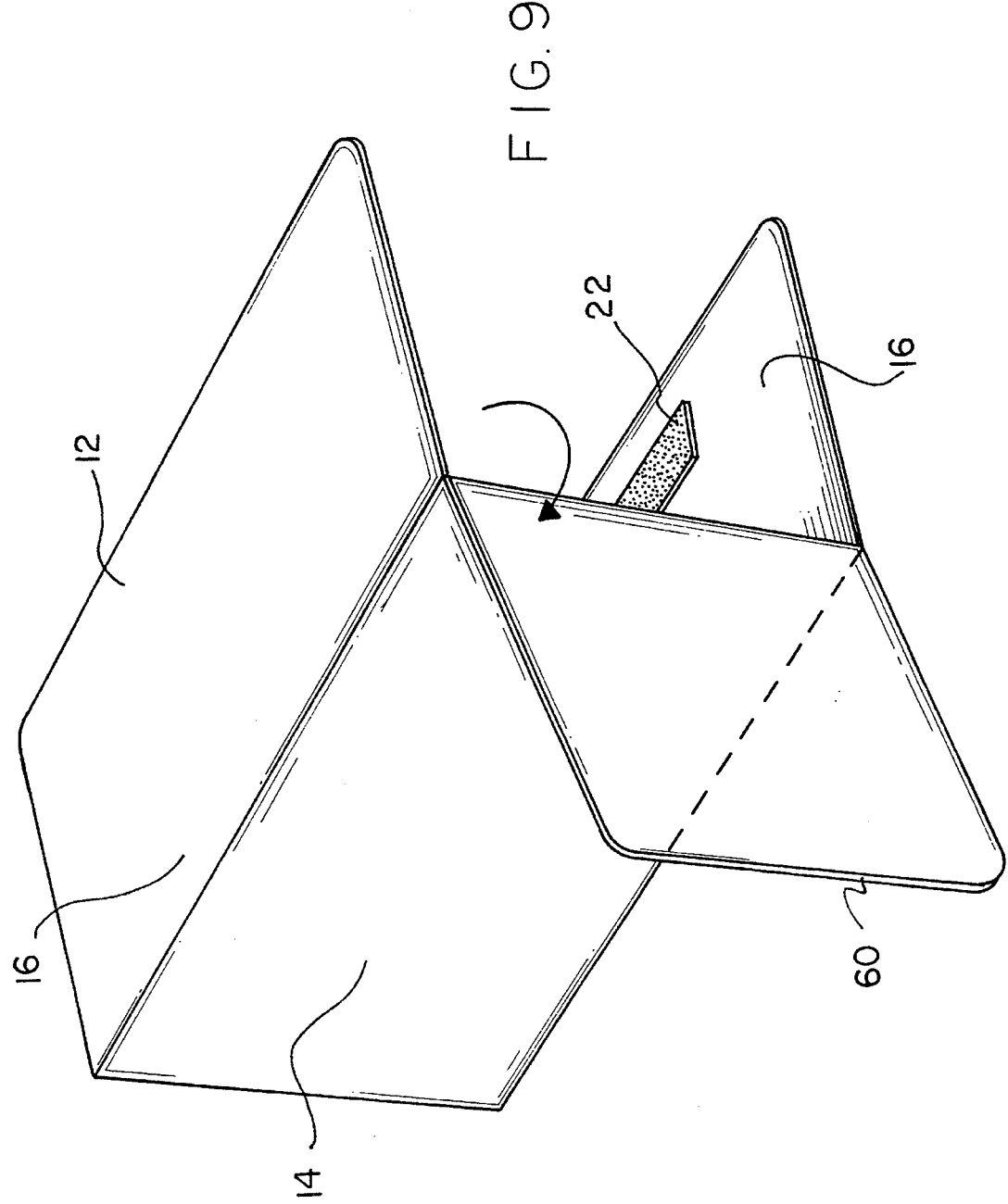

HAND IMMOBILIGING AND POSITIONING APPARATUS FOR X-RAY EXAMINATIONS

BACKGROUND OF THE INVENTION

1. Field of the Invention

The present invention relates generally to the field of devices for holding parts of the body in position while taking intra-operative radiographs in the surgical suite. More specifically, it relates to an apparatus for positioning the hand for antero-posterior and lateral views with minimal difficulty in reorienting the hand for each, and to isolate individual fingers for lateral views, so that the image of one finger is not superimposed over the image of an other finger. The apparatus is designed specifically for use in sterile environments where patient cooperation is not available. The apparatus includes a handreceiving channel member made of radiolucent material. The channel member has a bottom wall joined to two opposing side walls and is sized so that the back of the hand can be placed flat against the bottom wall. The apparatus also includes a block of radiolucent material, preferably formed of a foam plastic, sized to fit closely between the channel side walls, to hold any single extended finger against the channel bottom wall for lateral examination. The remaining fingers rest against a side face of the block and are curled generally toward the palm of the hand. The block and channel side walls are provided with fastening means which are preferably contact-activated, such as hook and loop fasteners or an adhesive, to removably secure the block within the channel member against the isolated finger during examination. The palm of the hand is preferably held within the channel member by securing straps. The apparatus alternatively includes a stepped support plate having a stepped edge for placing within the channel member so that a single finger rests on each step. As a result, all fingers are laterally isolated simultaneously, each finger being held extended by a tubular containing member.

2. Description of the Prior Art

There have recently been several devices for holding a hand and individual fingers of a patient in desired positions for X-ray examination. These devices have variously been expensive and complex, requiring of patient assistance unavailable during surgery, and incapable of isolating one or more fingers for lateral examination.

One prior device is that of Eaton, U.S. Pat. No. 4,674,110, issued on Jun. 16, 1987, which discloses a hand and finger X-ray positioning device. Eaton includes a base board on which the palm of the hand and forearm are placed. Securing straps anchor the forearm and wrist to the base board. Several pegs are selectively fit into a grid of holes in the base board to separate and retain fingers in a splayed configuration. A problem with Eaton is that no fingers are isolated for lateral or side view X-ray examination. If a lateral view were taken, the fingers would appear behind and in front of each other, yielding a superimposed, confused image.

Burkhalter, et al., U.S. Pat. No. 3,715,587, issued on Feb. 6, 1973, reveals a limb holder and positioner for use with a bone mineral analyzer. Burkhalter includes a platform for supporting the forearm and hand with the hand placed palm down. An adjustable abutment ear or fin extends vertically upward from the platform to protrude between the middle fingers and steady the hand. A clamp is provided which includes an upper horizontal member with a curved arm receiving recess for placing on top of the forearm, and a vertical post extends through a port in the horizontal member. A dial-headed set screw extends through the member to abut and fasten the member at a desired vertical elevation on the post, either against the arm or elevated off the arm. A beam transmissive window/slot is provided in the platform for passing gamma rays directed through the arm or hand for bone mineral content analysis. A beam directing structure extends upward from an edge of the platform and over the arm and hand. A problem with Burkhalter is that it is not designed to isolate individual fingers for lateral radiographs. Another problem with Burkhalter is that it is complex, delicate, and expensive to manufacture. As a result, it would likely have to be used for more than one patient, thereby sacrificing the guarantee of sterility.

Pirela-Cruz, U.S. Pat. No. 5,136,743, issued on Aug. 11, 1992, teaches a device for positioning the distal radioulnar joint for medical examination. Pirela-Cruz includes a platform sized to receive a forearm and hand of a patient. A pair of upright blocks are mounted on the platform and are spaced apart from each other for receiving between them a patient's wrist. A pair of pivoting gripping members extends from each block toward an opposing pair of gripping members on the other block. The gripping members engage the wrist to hold it steady for examination of the distal radioulnar joint. A post extends perpendicularly from the platform for the patient to grip, to help steady the arm and hand. A problem with Pirela-Cruz is that an anaesthetized patient could not grip the post. Another problem is that individual fingers are not isolated for lateral X-ray examination. Another problem is that the members from which Pirela-Cruz is assembled would apparently have to be heavy gauge, making the device costly.

Endura extremity positioners, illustrated on page 103 of Cone Instruments brochure, Volume 10, dated 1992–93, and page 293 of Picker Health Care Products Buyer's Guide, Volume 6, are stepped structures for fanning a patient's fingers for examination. A problem with Endura is that the stepped member cannot be reoriented to switch hands. Thus these members are not ambidextrous. Another problem is that no retaining means are provided for holding fingers of an anesthetized patient in place and extended.

It is thus an object of the present invention to provide a hand and finger positioning and posing apparatus which is sufficiently inexpensive to be disposable after examination of a particular patient is completed.

It is another object of the present invention to provide such an apparatus which is simple and easy to understand and use, and does not require patient assistance or cooperation.

It is still another object of the present invention to provide such an apparatus which will reduce operating time, exposure to radiation due to repeat X-ray examinations and physician frustration by offering a quick method of securing desired hand poritions.

It is finally an object of the present invention to provide such an apparatus which is ambidextrous.

SUMMARY OF THE INVENTION

The present invention accomplishes the above-stated objectives, as well as others, as may be determined by a fair reading and interpretation of the entire specification.

An apparatus is provided for positioning the hand and fingers of a patient for antero-posterior or lateral X-ray examination, including structure for supporting the back of a hand and a selected finger of hand, structure for retaining the selected finger in an extended position against the structure for supporting, and for directing the remaining fingers of the hand away from the structure for supporting so that the selected finger is isolated for antero-posterior or lateral X-ray examination. The structure for supporting preferably includes a plate member having a substantially planar support surface. The structure for retaining preferably includes a first retaining surface of a retaining member and the structure for directing preferably includes a second retaining surface of the retaining member. The retaining member preferably includes a substantially rectangular parallelepiped member and the first and second retaining surfaces are substantially mutually perpendicular faces of the parallelepiped member. The retaining member is preferably removably secured to the structure for supporting by retaining member fastening elements. The fastening elements are preferably contact-activated. The structure for supporting preferably includes two substantially parallel and spaced apart side wall portions extending from the side edges of the support surface, and substantially perpendicular to the support surface between which the hand and retaining member are received and removably secured by the retaining member fastening elements and hand securing strap.

Alternative retaining members preferably include four tubular, or open channel with fastening tabs, finger containing members sized to fit closely around each finger, additionally including containing member fastening elements for removably securing the containing members against the support surface. The structure for directing preferably includes a directing member having an abutting end for abutting the support surface and an opposing stepped end having several step portions for each supporting one of the remaining fingers, so that the fingers are each isolated for lateral examination. The directing member preferably includes fastening elements at one end and on each step at the opposing end for securing the directing member to the support surface and to each of three of the tubular finger containing members. The containing members preferably include fastening elements for securing the containing members to the directing member. Each containing member preferably has a longitudinal slit for opening the containing member for lateral insertion of a finger. Straps are provided for holding a hand of a patient across the palm and against the structure for supporting. One side wall portion of the structure for supporting is preferably hinged to pivot away from the other to facilitate insertion of the retaining member.

The apparatus preferably includes a prop structure for holding the support surface substantially vertically on one side, the prop structure including two brace members hingedly joined together, and fastening elements for securing an edge of the plate member to one brace member and fastening elements for securing the other brace member to an opposing edge of the plate member.

A method is provided of positioning a finger of a hand for antero-posterior and lateral X-ray examination, using an apparatus described above, includes the steps of placing the back of a patient's hand on the support surface, securing the hand by strapping it to the support surface, extending a finger to be examined to rest against 'the support surface, placing the first retaining surface of the retaining member against the selected finger to hold the finger extended flat against the support surface, while the remaining fingers of the hand rest in an upward position against the second retaining surface. Another method is provided of positioning fingers of a hand for antero-posterior and lateral X-ray examination, using the apparatus described above, including the steps of placing the directing member onto the support surface, placing a patient's fingers in the containing members, and placing each of three fingers surrounded by the containing members against individual steps on the stepped end of the directing member.

BRIEF DESCRIPTION OF THE DRAWINGS

Various other objects, advantages, and features of the invention will become apparent to those skilled in the art from the following discussion taken in conjunction with the following drawings, in which:

FIG. 3 is a perspective view of the retaining block of the first embodiment.

FIG. 5 is a perspective view of the stepped member of the second preferred embodiment and its fastening means.

FIG. 7 is a perspective view of a resiliently closing finger containing member and its fastening means.

FIG. 9 is a view as in FIG. 8, illustrating the alternative prop structure.

DETAILED DESCRIPTION OF THE PREFERRED EMBODIMENTS

Figure 1:
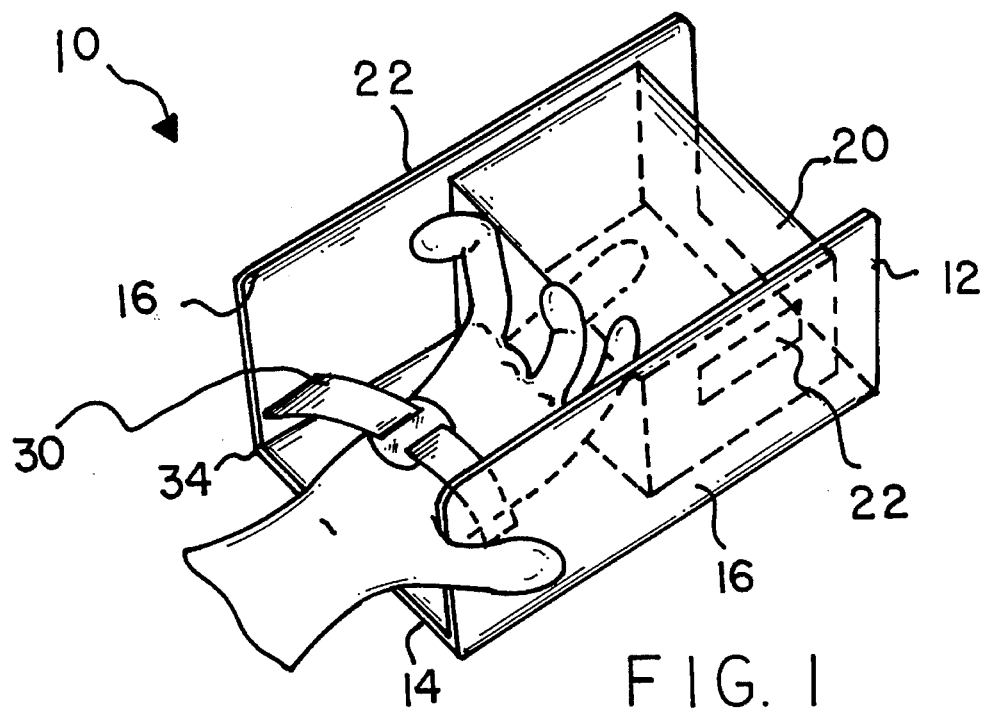
FIG. 1 is a perspective view of the first embodiment of the inventive positioning apparatus shown positioning a hand to isolate a selected finger for lateral examination.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
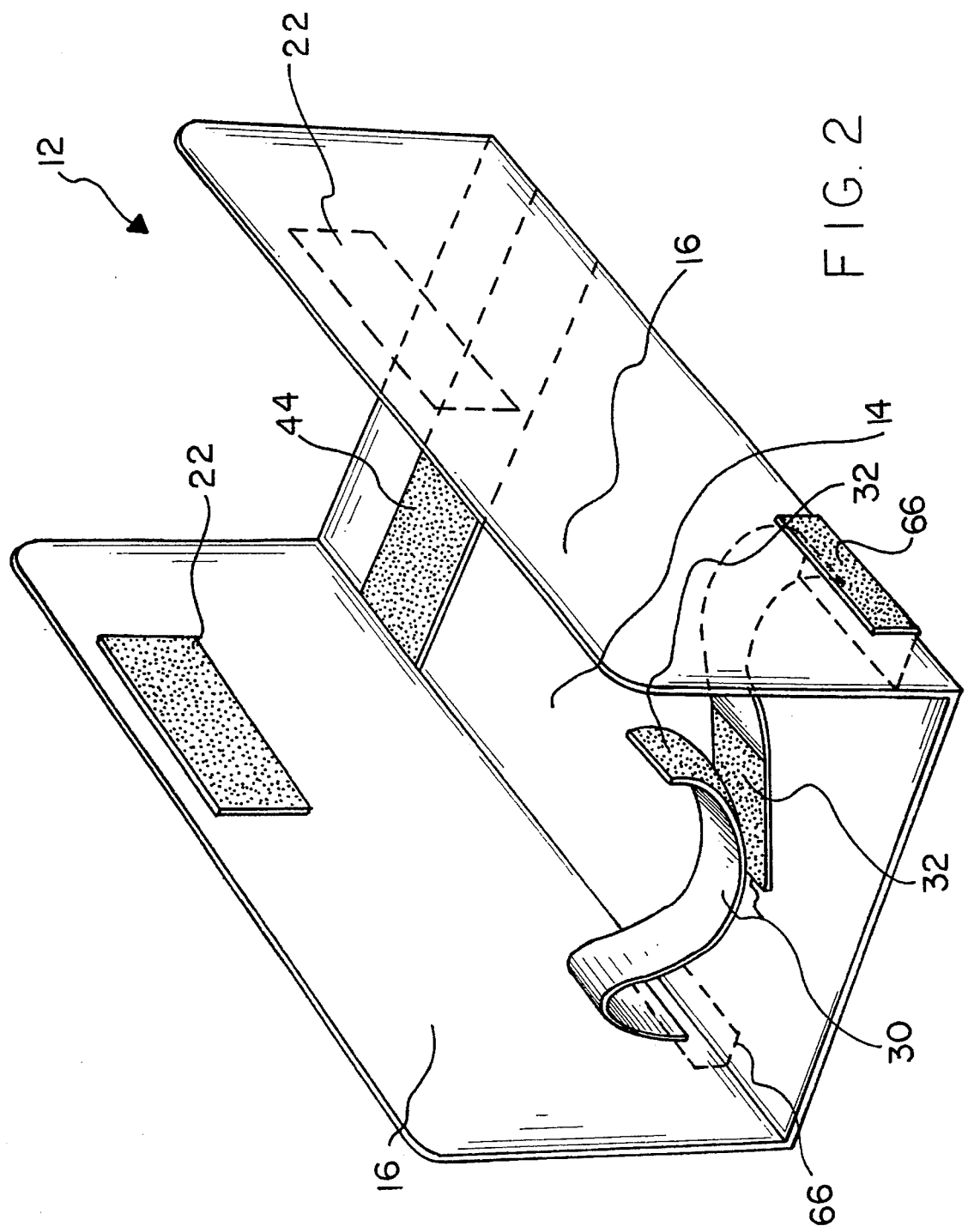
FIG. 2 is a perspective view of the channel member, channel fastening means and retaining straps only, with hidden portions shown in broken lines.
Figure 4:
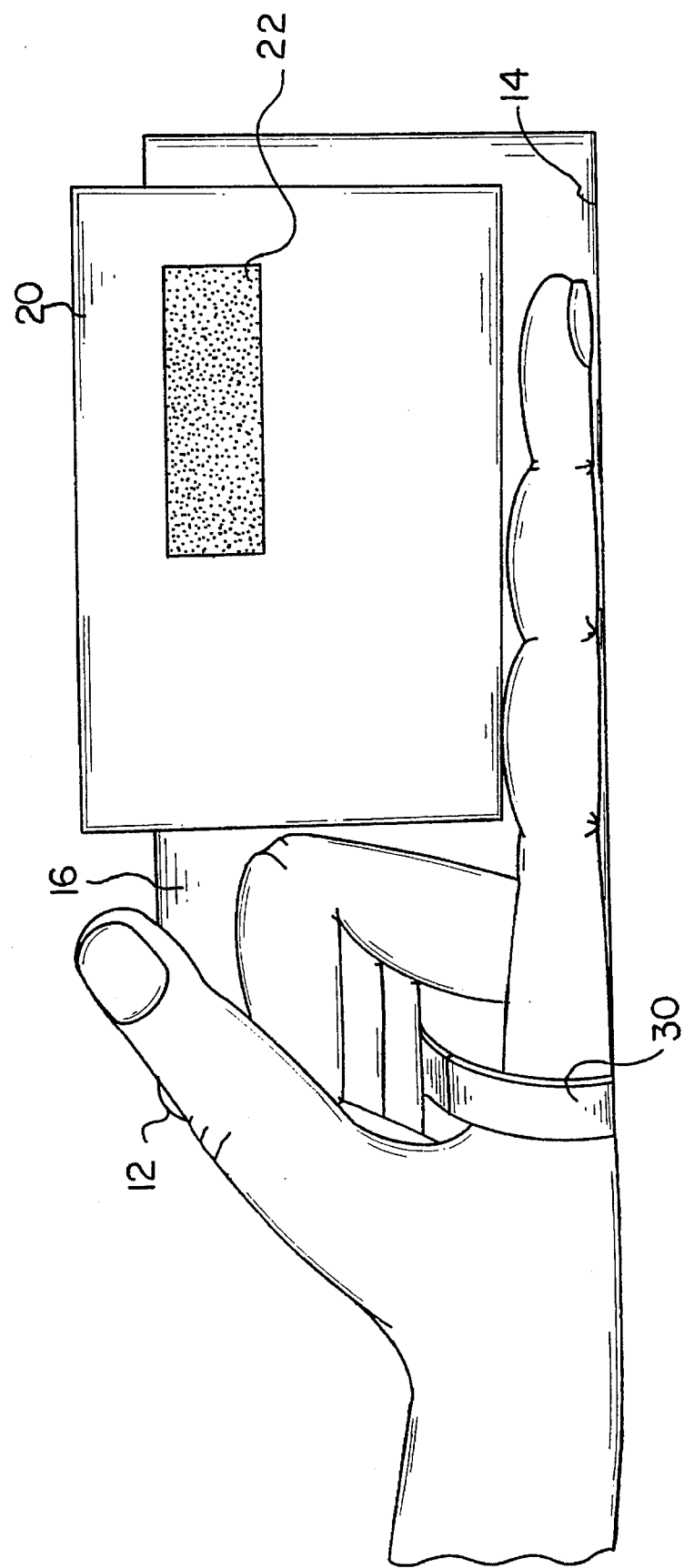
FIG. 4 is a side view of the first embodiment with a hinged channel side wall pivoted down to reveal the manner in which the retaining block isolates a finger within the channel member.

Referring to FIG. 1, an apparatus 10 is disclosed for retaining the hand and fingers of a patient under anesthesia in positions which isolate individual fingers for unobstructed lateral radiographs. Apparatus 10 preferably includes a hand-receiving channel member 12 formed of X-ray transparent, also known as radiolucent, material. See FIG. 2. Channel member 12 has a bottom wall 14 and two opposing, parallel side walls 16 extending upward therefrom, and is sized to receive the back of an average patient's hand flat against bottom wall 14. Apparatus 10 also includes a block 20 of X-ray transparent material, preferably fabricated from a foam plastic and sized to fit closely between side walls 16. See FIG. 3. Block 20 holds a single finger flat against bottom wall 14 for lateral examination, while the remaining fingers rest against a side face of block 20. See FIG. 4.

Block 20 and channel side walls 16 are preferably provided with contact-activated fastening means 22, respectively. See FIGS. 2 and 3. Fastening means 22 and all other fastening means hereinafter identified are preferably hook and loop fastener strips such as that known as VELCRO™. Fastening means 22 removably secure block 20 to channel member 12 side walls 16. Channel walls 16 either resiliently bend outward to permit insertion of block 20 and resiliently return with elastic memory to make contact with and engage block 20, or one may be hingedly mounted to channel bottom wall 14. Alternatively, an adhesive, snap fasteners, or other suitable fastening means may be used to removably secure block 20 within channel member 12, in place of other fastening means identified below. The patient's hand is preferably secured across the palm within channel member 12 by securing straps 30. Straps 30 wrap over the hand and engage each other with patches of contact-activated fastening means 32, or with a buckle 34, a knot, or an equivalent structure. See FIGS. 1 and 2.

Second Preferred Embodiment

Figure 6:
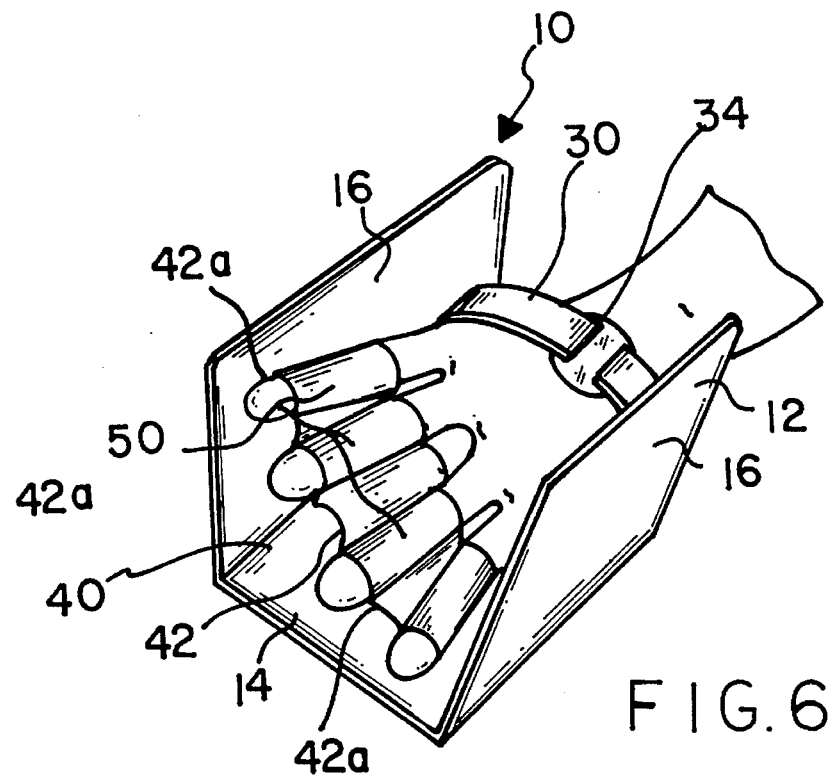
FIG. 6 is a perspective view of the second preferred embodiment of the inventive positioning apparatus shown positioning a hand to isolate all fingers for simultaneous lateral examination.

For examinations requiring isolation and examination of all fingers simultaneously, apparatus 10 alternatively includes a stepped support member 40 having a stepped edge 42, and includes tubular members 50. See FIGS. 5 and 6. For an antero-posterior view, containing members 50 are laid flat on bottom wall 14 open side upward. The hand may be strapped into channel member 12 and then each finger is placed and secured in the containing member 50, described below. Then, member 40 is inserted into channel member 12 in place of block 20 so that a single finger rests on each step 42a, with the exception of an end finger secured flat on channel bottom wall 14. Member 40 is secured against channel bottom wall 14 with fastening means 44. Member 40 serves to fan the fingers so that all fingers can be laterally radiographed simultaneously, with none superimposed over another. Member 40 is simply rotated one-half turn about its vertical axis 40A to orient it for fanning fingers on the other hand, and thus, like the rest of apparatus 10, it is ambidextrous. Contact-activated fastening means 44 may additionally hold stepped member 40 in place within channel member 12, angled so as to mate with fastening means on bottom wall 14 and containing members 50.

Tubular finger containing members 50 each receive a single finger for holding the finger in an extended position. See FIGS. 6 and 7. Fastening means 52, which are preferably contact-activated fastening means, are provided on each step 42a. A mating portion of fastening means 52 is provided on each containing member 50 to engage fastening means 52 and hold the fingers in place on steps 42a during examination. Containing members 50 preferably each have an axially directed lateral slit 54 so that they can be opened and laterally wrapped around a finger. Slit 54 may be located adjacent to a hinged portion of the member 50 side wall such that the hinged portion may be opened to admit a finger, then closed and locked against a tab portion to retain the finger, and opened again to release the finger. Alternatively, the edges of each slit 54 may overlap due to the resilience of the radiolucent member 50 material, and the resilience automatically closes members 50 around the fingers. Contact-activated fastening means 56 are provided along slits 54 to hold members 50 closed. Containing members 50 are preferably optically transparent to permit viewing of the fingers during positioning to confirm proper orientation for examination.

Figure 8:
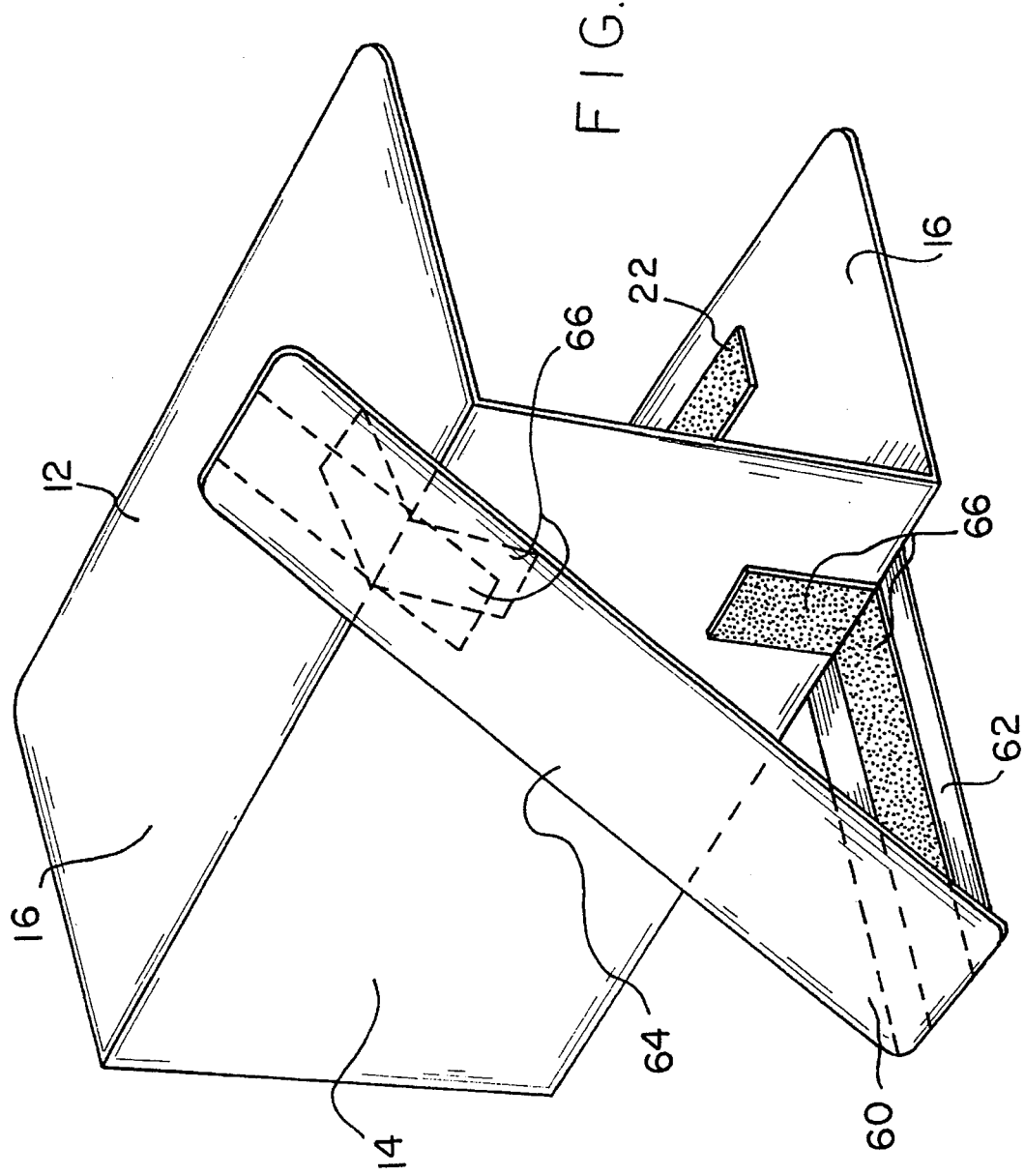
FIG. 8 is a perspective view of the channel member secured on its side by the inventive prop structure. The channel member may be turned to rest on either side to accomodate right or left hand lateral views.

A channel member 12 prop structure 60 is preferably provided for holding channel member 12 on one of its sides to permit a vertically directed X-ray beam for lateral examination. Prop structure 60 preferably takes the form of a base plate 62 onto which a side wall 16 of channel 12 is placed and secured with fastening means 66 on channel member 12 and on plate 62. A hinged portion 64 pivotally extends upward from base plate 62 to touch and engage a channel member 12 upper portion with contact-activated fastening means 66 provided on portion 64 and on channel member 12. See FIG. 8. Alternatively, a hinged portion of bottom wall 14 equal in width and of sufficient length that when pivoted to position substantially perpendicular to bottom wall 14 might serve to maintain the vertical positioning of bottom wall 14. See FIG. 9.

It should be noted that both above-described embodiments of apparatus 10 are fully ambidextrous. In addition, the corners of apparatus 10 are preferably rounded for safety and to prevent accidental puncture of X-ray cassette drapes or bags used in maintaining a sterile field. All elements and parts of apparatus 10 are preferably radiolucent, and many are necessarily radiolucent.

Method

In practicing the invention, the following method may be used. The back of a patient's open hand is placed in channel member 12 against bottom wall 14. The hand is strapped into channel member 12 with straps 30. A finger to be examined is extended to rest against bottom wall 14, and block 20 is placed in channel member 12 and against the selected finger to hold the finger extended flat against bottom wall 14. The remaining fingers rest in an upward, curled position against a vertical side of block 20.

Alternatively, for multiple finger examination, for the antero-posterior view, containing members 50 are placed flat on bottom wall 14 with open side upward and fastening means 52 engaged with fastening means 44. The hand is then strapped into channel member 12 with the palm upward and each finger is placed and secured in a containing member 50. Then for the lateral view, the index, middle, and ring fingers, each remaining in their containing members, are unfastened from fastening means 44, stepped member 40 is placed into channel member 12 with the longest step adjacent to the index finger and fastened therein with fastening means 44, then each of these three fingers, within its containing member 50 is placed on the upper surface of each corresponding step 42a and fastened in place with fastening means 52.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. An apparatus for positioning and immobilizing the hand and fingers of a patient, wherein said fingers comprise all fingers other than the thumb, for antero-posterior and lateral X-ray examination of said selected finger, comprising:

means for supporting having a supporting surface for supporting the back of a hand and a selected finger of said hand, a finger directing member having an abutting end for abutting said support surface and an opposing stepped end having a plurality of step portions for each supporting one of said fingers, such that said steps are each at position laterally distinct from all other said steps and wherein said steps are of sufficient size and are sufficiently staggered to spread said fingers sufficiently to isolate all said fingers on said steps for lateral X-ray examination.

2. The apparatus of claim 1, additionally comprising a finger retaining means for retaining said fingers on said steps.

3. The apparatus of claim 2, wherein said finger retaining means comprises a tubular finger containing member sized to fit closely around one said finger, additionally comprising containing member fastening means for removably securing said containing member against one of said steps.

4. The apparatus of claim 3, wherein said containing member has a longitudinal slit for opening said containing member for lateral insertion of a finger.

5. The apparatus of claim 3, wherein said containing member has a pivoting side wall portion which pivots open to receive a finger and pivots closed to retain said finger.

* * * * *